US012571784B2

(12) United States Patent
Li et al.

(10) Patent No.: US 12,571,784 B2
(45) Date of Patent: Mar. 10, 2026

(54) GAS MEASURING APPARATUS

(71) Applicant: Nova Skantek Instruments (Beijing) Co., Ltd., Beijing (CN)

(72) Inventors: Chao Li, Beijing (CN); Hanguang Xue, Beijing (CN)

(73) Assignee: Nova Skantek Instruments (Beijing) Co., Ltd., Beijing (CN)

( * ) Notice: Subject to any disclaimer, the term of this patent is extended or adjusted under 35 U.S.C. 154(b) by 411 days.

(21) Appl. No.: 18/031,448

(22) PCT Filed: Nov. 3, 2021

(86) PCT No.: PCT/CN2021/128392
§ 371 (c)(1),
(2) Date: Apr. 12, 2023

(87) PCT Pub. No.: WO2022/100494
PCT Pub. Date: May 19, 2022

(65) Prior Publication Data
US 2023/0408471 A1 Dec. 21, 2023

(30) Foreign Application Priority Data

Nov. 16, 2020 (CN) .......................... 202011274946.9
Nov. 16, 2020 (CN) .......................... 202022647858.0

(51) Int. Cl.
| G01N 33/00 | (2006.01) |
| G01F 15/08 | (2006.01) |
| G01F 15/18 | (2006.01) |

(52) U.S. Cl.
CPC ......... *G01N 33/0022* (2013.01); *G01F 15/08* (2013.01); *G01F 15/18* (2013.01); *G01N 33/0014* (2013.01)

(58) Field of Classification Search
CPC ........... G01N 33/0022; G01N 33/0014; G01F 15/08; G01F 15/18
(Continued)

(56) References Cited

FOREIGN PATENT DOCUMENTS

| CN | 203271718 U | 11/2013 | |
| CN | 106092235 A | * 11/2016 | ............... G01F 3/28 |

(Continued)

OTHER PUBLICATIONS

Wang Xianhuan, <<Aerated Flow in Hydraulic Structures>>, 1st edition, Aug. 31, 1984, p. 6-7, China Water Resources and Hydropower Press, Beijing, China.

*Primary Examiner* — Peter J Macchiarolo
*Assistant Examiner* — Rodney T Frank

(57) ABSTRACT

A gas measuring apparatus (100), including: a gas collecting device (102), including two gas entrapping compartments (1021, 1022); a fixing frame (103), which is rotatably connected with the gas collecting device (102); positioning holders (104, 105), each of which is located below a corresponding one of the two gas entrapping compartments (1021, 1022) and is configured to limit the rotation angle of the gas collecting device (102) by colliding with an edge of the corresponding one of the gas entrapping compartments (1021, 1022); a chamber (101), which accommodates the gas collecting device (102), the fixing frame (103), the positioning holders (104, 105) and a liquid medium; and a gas inlet (106), which is located below the gas collecting device (102). The apparatus (100) solves the problem of relatively low accuracy of measurement results.

16 Claims, 12 Drawing Sheets

(58) Field of Classification Search
USPC .......................................................... 73/23.2
See application file for complete search history.

(56)                    References Cited

FOREIGN PATENT DOCUMENTS

| CN | 205940667 U | | 2/2017 | | |
|---|---|---|---|---|---|
| CN | 206132149 U | | 4/2017 | | |
| CN | 206833019 U | | 1/2018 | | |
| CN | 110030428 A | | 7/2019 | | |
| CN | 209559277 U | | 10/2019 | | |
| CN | 211205409 U | * | 8/2020 | .............. | G01F 11/26 |
| EP | 3663011 A1 | | 6/2020 | | |
| JP | 2003295006 A | | 10/2003 | | |

* cited by examiner

GAS MEASURING APPARATUS

CROSS-REFERENCE TO RELATED APPLICATION

This patent application is a national stage application of International Patent Application No. PCT/CN2021/128392, filed on Nov. 3, 2021, which claims priorities of Chinese Patent Application No. 202011274946.9, filed on Nov. 16, 2020, and Chinese Patent Application No. 202022647858.0, filed on Nov. 16, 2020, the disclosures of which are incorporated by reference herein in their entities.

TECHNICAL FIELD

The present disclosure relates to the technical field of gas measurement, in particular to a gas measuring apparatus.

BACKGROUND

The measuring structures of the existing gas measuring apparatuses are mostly single-cavity structures. The single cavity is immersed in the initial position of a liquid medium in an inverted manner, and gas enters the single cavity in the form of bubbles from the opening below the single cavity, thus realizing the collection of gas by the single cavity. When the collected gas reaches the preset capacity, the buoyancy generated by the gas is greater than the force required for lifting the single cavity, so that the single cavity is lifted close to the liquid level of the liquid medium, and the gas overflows into air from the single cavity, thereby, the buoyancy of the single cavity is reduced, and the single cavity falls back to the initial position under the action of gravity. The gas to be measured is continuously flow in, as it takes a certain time for the single cavity lifted and then fall back into place, resulting in the leakage of the gas to be measured. The gas cannot be collected by the single cavity, so that the accuracy of gas measurement results is low.

SUMMARY

In view of this, embodiments of the present disclosure provide a gas measuring apparatus, which solves the problem of inaccurate measurement of ultra low gas flow.

An embodiment of the present disclosure provides a gas measuring apparatus, including: an inverted bucket, including a pair of gas entrapping compartments; a fixing frame, which is rotatably connected with the gas collecting device; positioning holders, each of which is located below a corresponding one of the two gas entrapping compartments and is configured to limit the rotation angle of the gas collecting device by colliding with an edge of the corresponding one of the gas entrapping compartments; a chamber, which accommodates the gas collecting device, the fixing frame, the positioning holders and a liquid medium; and a gas inlet, which is located below the gas collecting device, where bubbles emerge from the gas inlet and rise into one of the two gas entrapping compartments, as the bubbles accumulate, the liquid medium in the one of the two gas entrapping compartments is gradually discharged, and the gas collecting device rotates under the buoyancy effect of the bubbles which are accumulated, so that the bubbles emerged from the gas inlet rise into an other one of the two gas entrapping compartments.

In an embodiment of the present disclosure, the two gas entrapping compartments may be symmetrically arranged.

In an embodiment of the present disclosure, each of the positioning holders may include: a fixing unit, which may be fixedly connected with the fixing frame; and a stroke adjusting unit, which may be located above the fixing unit and may be movably connected to the fixing unit up and down, so as to realize the height adjustment of a corresponding one of the positioning holders and adjust the collision position with a corresponding one of the two gas entrapping compartments.

In an embodiment of the present disclosure, the gas collecting device may further include: a partition, which may be configured to separate the two gas entrapping compartments, so as to realize the symmetrical separation of the two gas entrapping compartments; and a bubble steering unit, which may include a sheet structure or a block structure, the bubble steering unit may be fixedly connected to the partition of the two gas entrapping compartments for blocking a deviation of a rising route of the bubbles.

In an embodiment of the present disclosure, a cross section of the bubble steering unit parallel to a side wall of the gas collecting device may be of an inverted triangle shape.

In an embodiment of the present disclosure, the gas inlet may include a circular through-hole, one end of the gas inlet may be connected with one end of a gas inlet pipeline, and gas enters from an other end of the gas inlet pipeline and emerges from an other end of the gas inlet; where the diameter of the circular through-hole may be smaller than an internal diameter of the gas inlet pipeline.

In an embodiment of the present disclosure, the gas collecting device may further include: a partition, which may be configured to separate the two gas entrapping compartments, so as to realize the symmetrical separation of the two gas entrapping compartments; a rod-shaped structure, one end of which may be connected with the partition and swings with the gas collecting device; and a transmitter, which may be fixedly installed at an other end of the rod-shaped structure and may be configured to send a swing signal of the gas collecting device.

In an embodiment of the present disclosure, an outline of the rod-shaped structure may be streamlined.

In an embodiment of the present disclosure, the measuring apparatus may further include: a receiver, which may communicate with the transmitter and may receive the swing signal sent by the transmitter.

In an embodiment of the present disclosure, the receiver may be located outside the chamber; where an inner bottom surface of the chamber may include a concave part, and the concave part provides an accommodation space for one end of the rod-shaped structure where the transmitter may be installed, so that the rod-shaped structure passes through the concave part when swinging to a bottom of the chamber.

In an embodiment of the present disclosure, a material of the chamber may include a transparent material.

In an embodiment of the present disclosure, the chamber may include: a curved strip-like depression, which may be located at an outer side of the chamber; where an outline of a cross section of the curved strip-like depression perpendicular to the chamber includes an arc line.

In an embodiment of the present disclosure, the apparatus may further include: a pipeline guiding unit, which may be fixedly connected with the fixing frame, where the pipeline guiding unit may include a tubular structure and/or a groove-shaped structure for surrounding and/or semi-surrounding the gas inlet pipeline, so that the gas inlet pipeline may be laid along the pipeline guiding unit.

In an embodiment of the present disclosure, the apparatus may further include: a gas outlet, which may be located at the upper part of the chamber and may be configured to release the gas emerged from the liquid medium.

According to the gas measuring apparatus provided by the embodiments of the present disclosure, two gas entrapping compartments are provided, so that bubbles emerged from the gas inlet enter one of the two gas entrapping compartments, and when the gas collecting device rotates to release the gas in the gas entrapping compartment after the accumulated bubble volume reaches a certain level, the bubbles emerged from the gas inlet enter the other one of the two gas entrapping compartments in turn, thus the gas leakage is avoided and the accuracy of gas measurement results are improved. In addition, the positioning holders are provided, so that the rotation angle of the gas collecting device can be limited, thus the center of gravity position of the gas collecting device when rotate to a preset angle is accurately limited, the buoyancy of the gas required for rotating the gas collecting device is accurately limited, and the volume of the gas in the gas entrapping compartment corresponding to one rotation is accurately limited, so as to further improve the accuracy of the gas measurement.

DETAILED DESCRIPTION OF THE EMBODIMENTS

The technical solutions in the embodiments of the present disclosure will be clearly and completely described below with reference to the drawings in the embodiments of the present disclosure. Obviously, the described embodiments are only part of the embodiments of the present disclosure, rather than all of the embodiments. Based on the embodiments in the present disclosure, all other embodiments obtained by those skilled in the art without creative effects belong to the scope of protection in the present disclosure.

Figure 1:
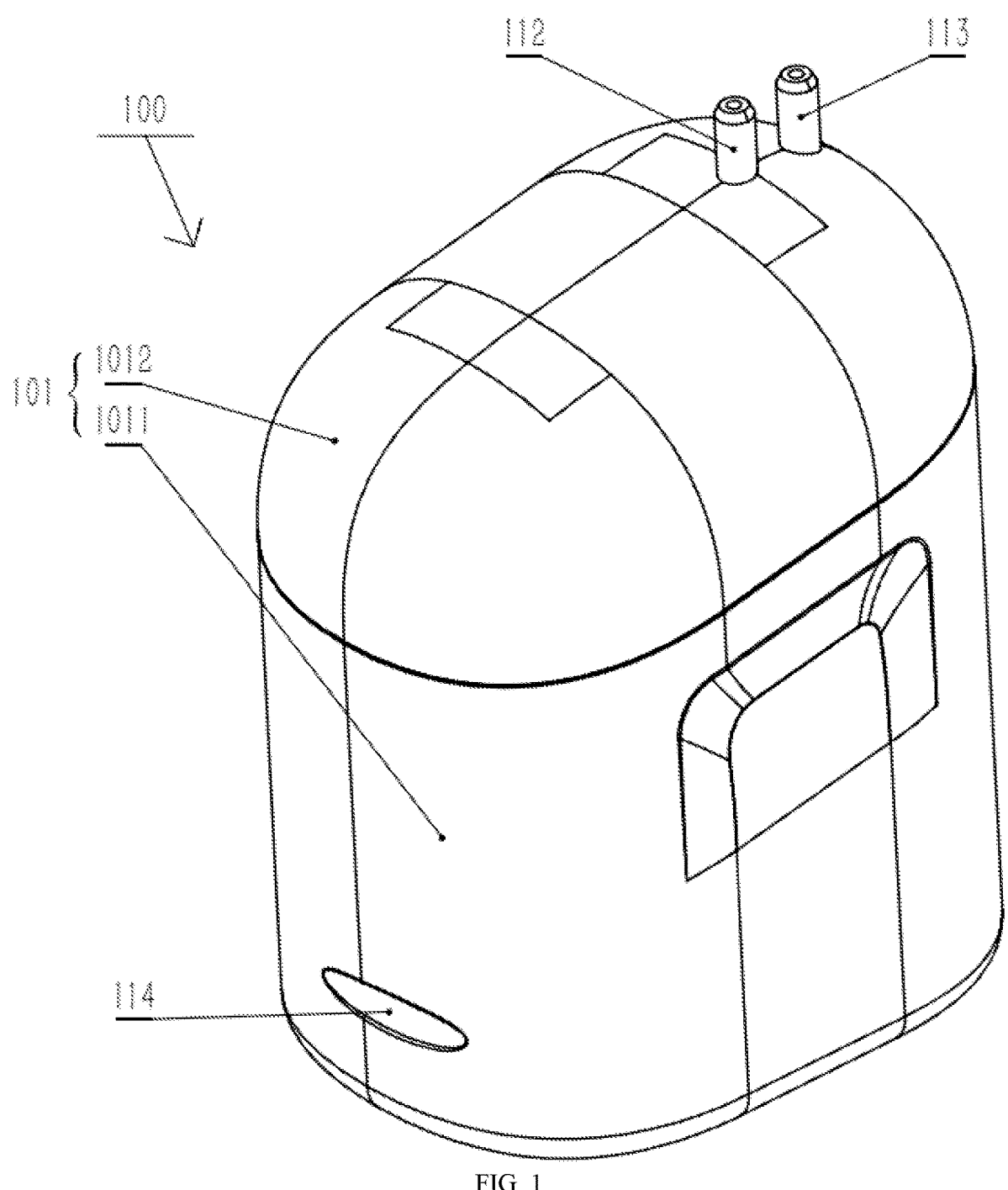
FIG. 1 is a schematic structural diagram of a gas measuring apparatus according to embodiments of the present disclosure.
Figure 2:
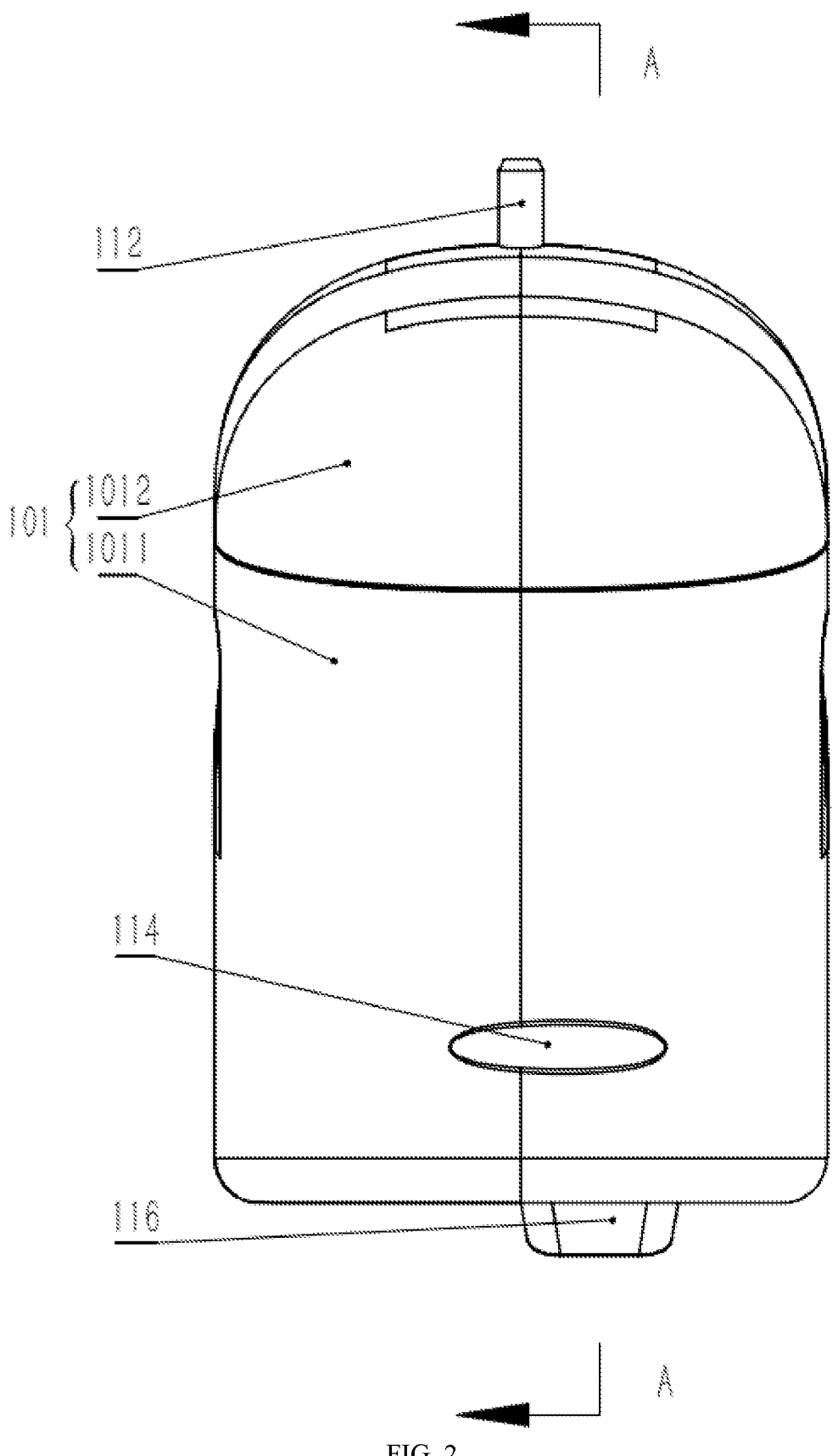
FIG. 2 is a front view of a gas measuring apparatus according to embodiments of the present disclosure.
Figure 3:
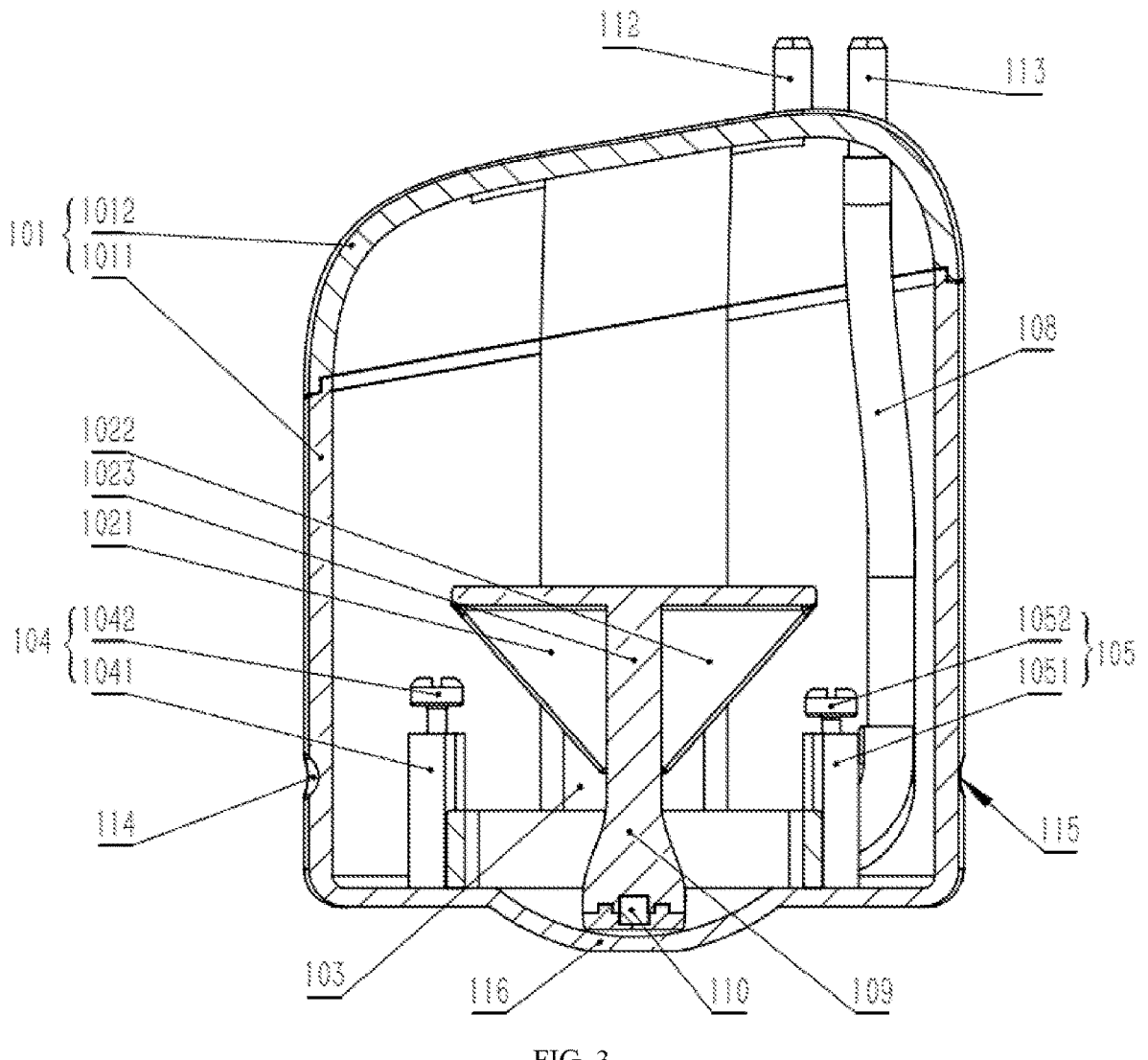
FIG. 3 is a sectional view of section A-A in embodiments shown in FIG. 2.
Figure 4:
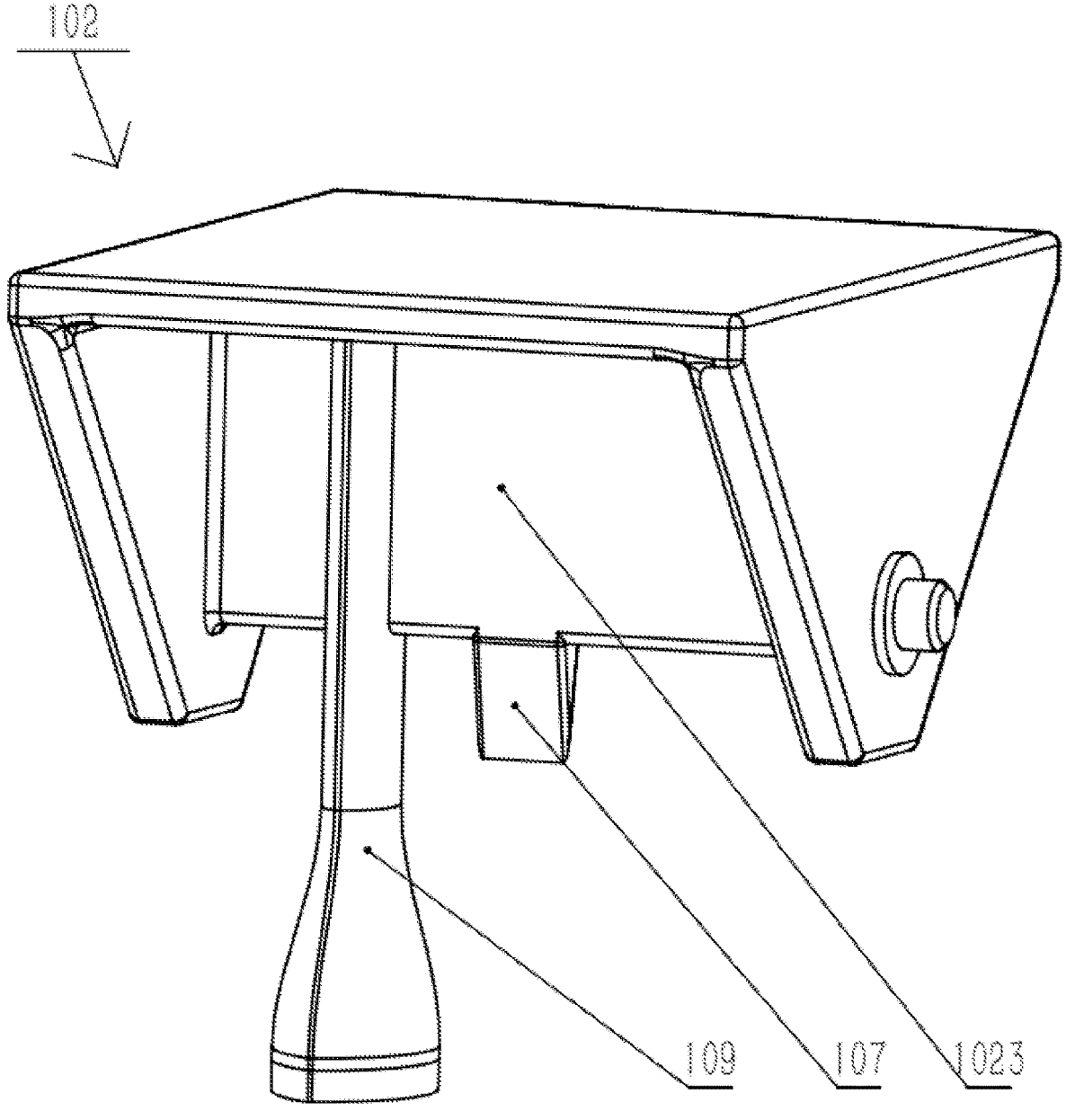
FIG. 4 is a schematic structural diagram of a gas collecting device according to embodiments of the present disclosure.
Figure 5:
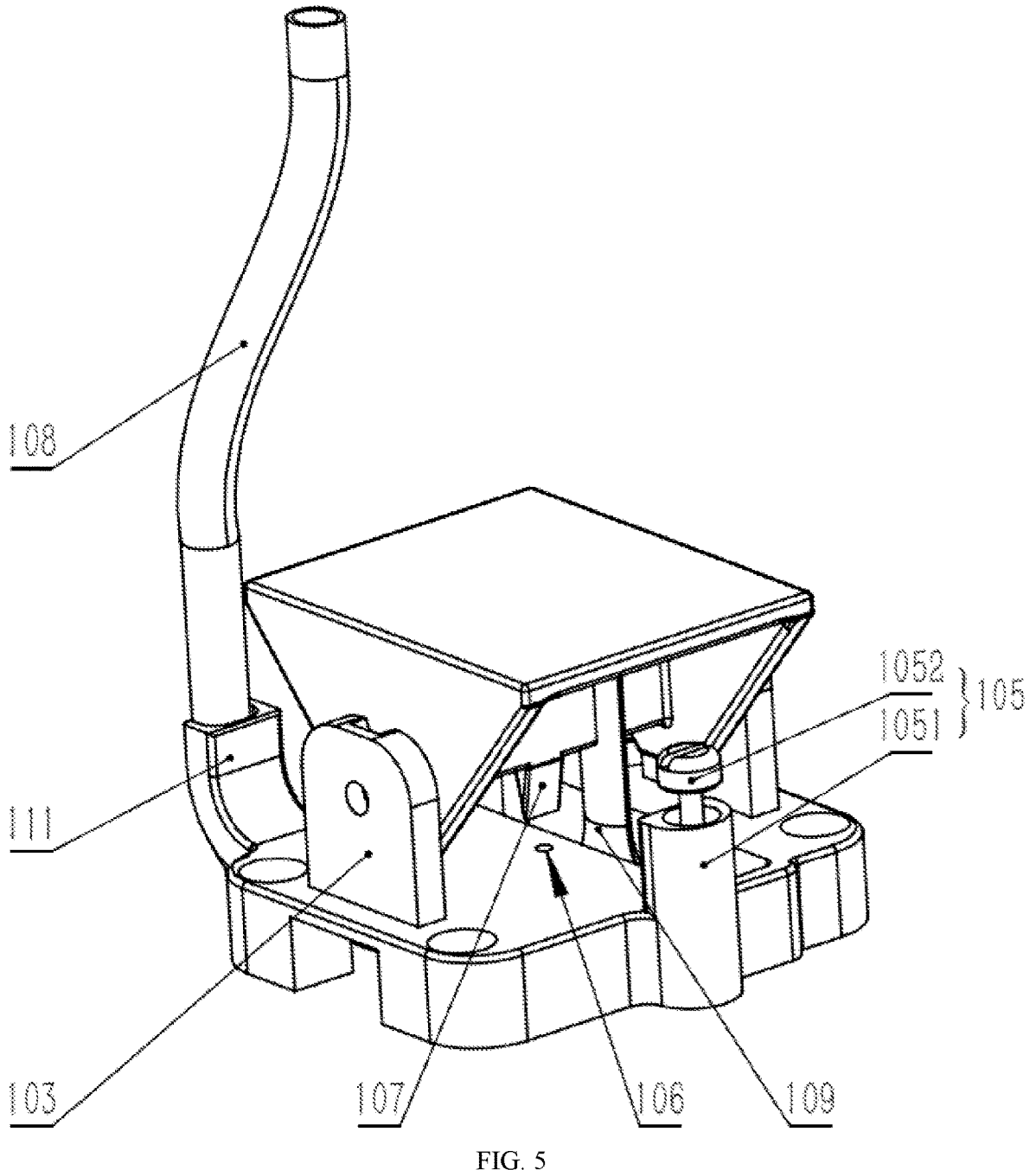
FIG. 5 is a schematic structural diagram of a gas measuring apparatus according to embodiments of the present disclosure with a chamber removed.
Figure 6:
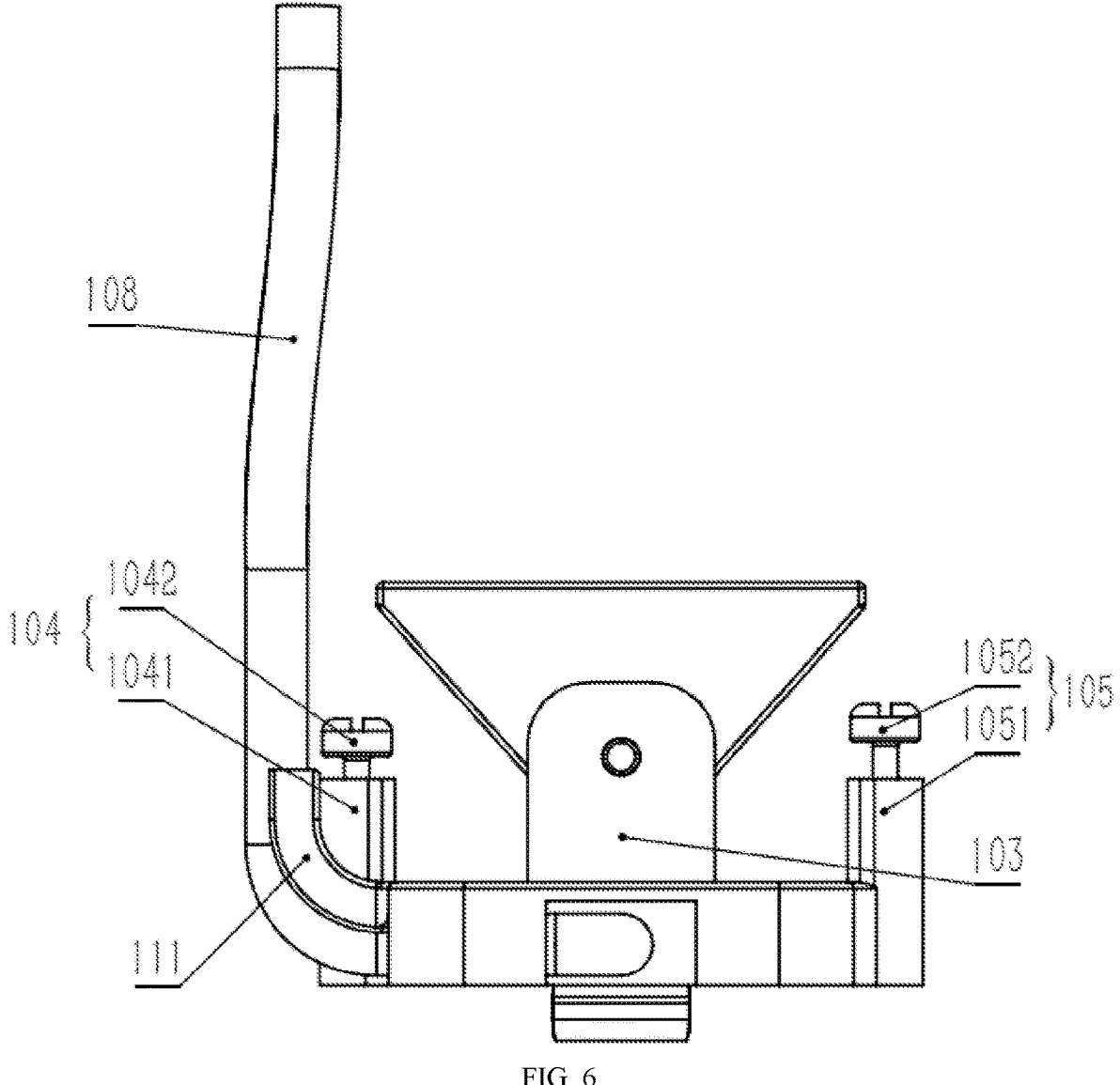
FIG. 6 is a left side view of a gas measuring apparatus according to embodiments of the present disclosure with a chamber removed.
Figure 7:
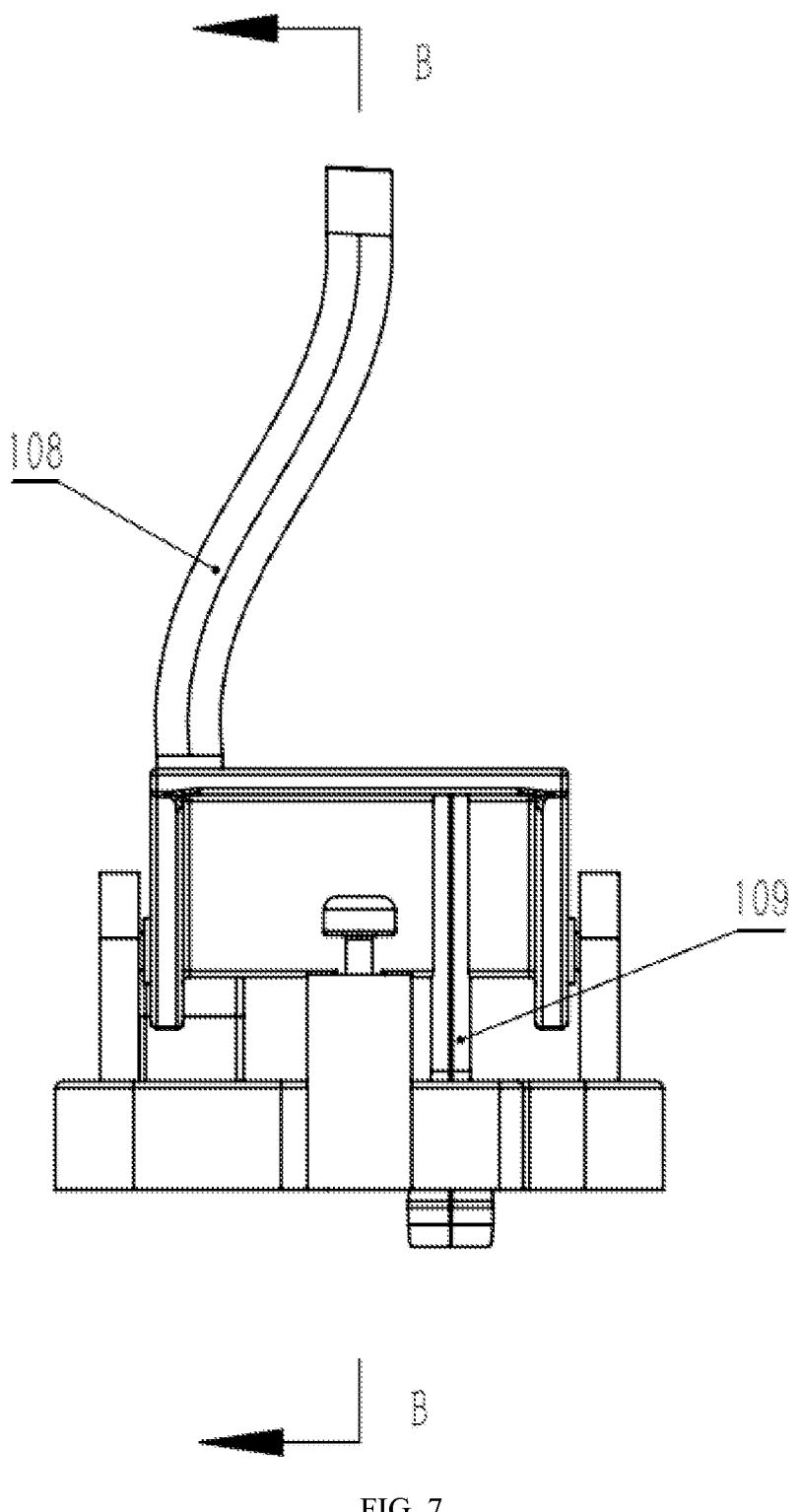
FIG. 7 is a front view of a gas measuring apparatus according to embodiments of the present disclosure with a chamber removed.
Figure 8:
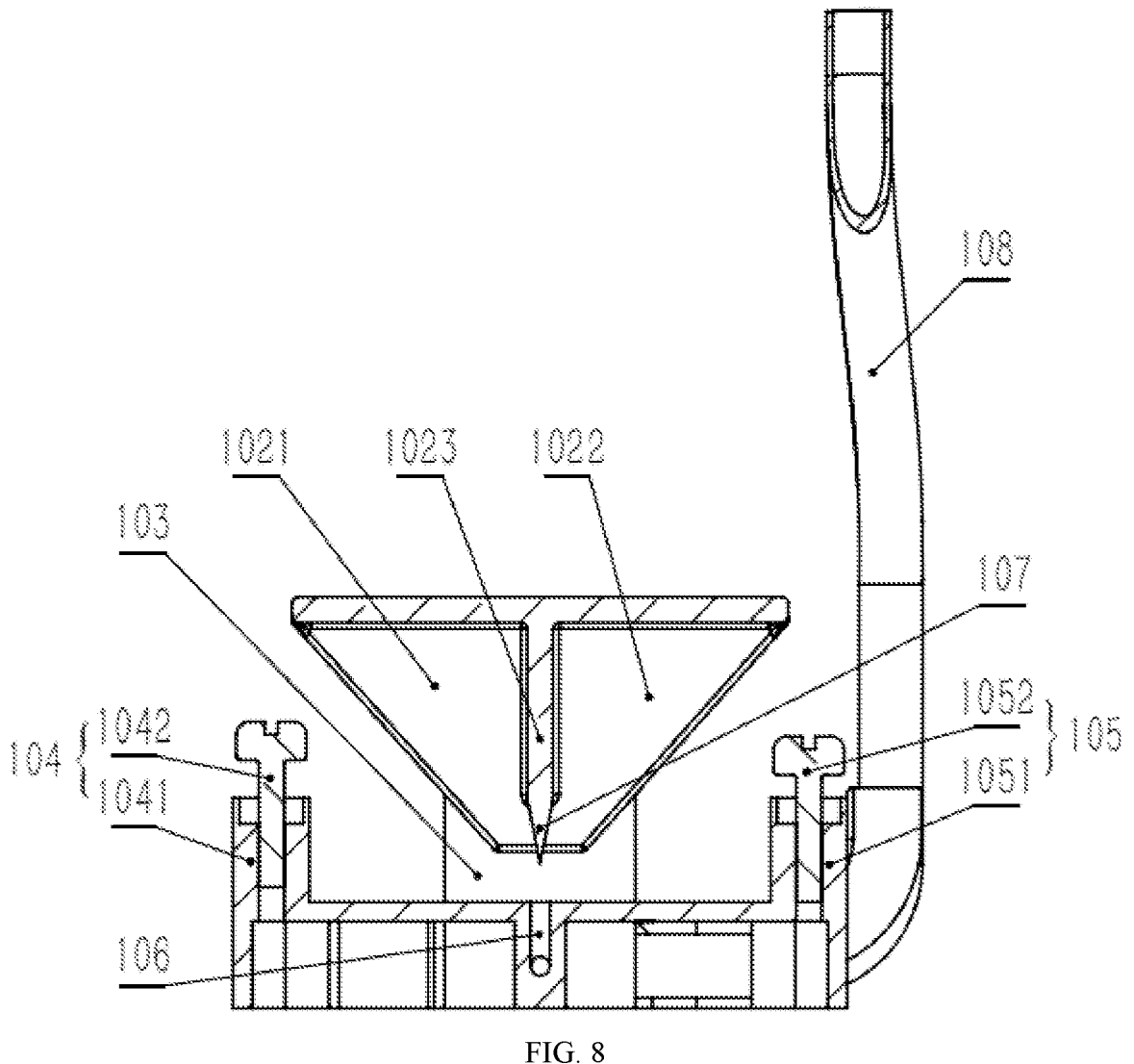
FIG. 8 is a sectional view of section B-B in embodiments shown in FIG. 7.

FIG. 1 is a schematic structural diagram of a gas measuring apparatus according to embodiments of the present disclosure. FIG. 2 is a front view of a gas measuring apparatus according to embodiments of the present disclosure. FIG. 3 is a sectional view of section A-A in embodiments shown in FIG. 2. FIG. 4 is a schematic structural diagram of a gas collecting device according to embodiments of the present disclosure. FIG. 5 is a schematic structural diagram of a gas measuring apparatus according to embodiments of the present disclosure with a chamber removed. FIG. 6 is a left side view of a gas measuring apparatus according to embodiments of the present disclosure with a chamber removed. FIG. 7 is a front view of a gas measuring apparatus according to embodiments of the present disclosure with a chamber removed. FIG. 8 is a sectional view of section B-B in embodiments shown in FIG. 7. As shown in FIGS. 1-8, the gas measuring apparatus 100 includes a chamber 101, a gas collecting device 102, a fixing frame 103, a first positioning holder 104, a second positioning holder 105, and a gas inlet 106. The gas collecting device 102 includes a first gas entrapping compartment 1021 and a second gas entrapping compartment 1022. The fixing frame 103 is rotatably connected with the gas collecting device 102. The first positioning holder 104 is located below the first gas entrapping compartment 1021, and the second positioning holder 105 is located below the second gas entrapping compartment 1022. The first positioning holder 104 and the second positioning holder 105 are configured to limit the rotation angle of the gas collecting device by colliding with the edges of the first gas entrapping compartment 1021 and the second gas entrapping compartment 1022 respectively. The chamber 101 is configured to accommodate the gas collecting device 102, the fixing frame 103, the first positioning holder 104, the second positioning holder 105 and the liquid medium. The gas inlet 106 is located below the gas collecting device 102, and bubbles emerge from the gas inlet 106 and rise into one of the two gas entrapping compartments. As the bubbles accumulate, the liquid medium in the one of the two gas entrapping compartments is gradually discharged, and the gas collecting device 102 rotates under the buoyancy effect of the accumulated bubbles, so that the bubbles emerged from the gas inlet rise into an other one of the two gas entrapping compartments. This cycle is repeated until the measurement stops.

The gas measuring apparatus 100 is a apparatus that accumulates a preset volume of gas through circulation, releases the gas and counts the volume of the gas. By multiplying the counted number of rotations by the preset volume, the gas volume flowing through the gas measuring apparatus 100 can be obtained. The preset volume can be the preset resolution of the gas measuring apparatus 100, that is, the threshold value of the gas contained in each of the two gas entrapping compartments. When the volume of the gas contained in one of the two gas entrapping compartments is larger than the preset volume, the buoyancy generated by the bubbles 119 is larger than the rotating force of the gas collecting device 102, so that the gas collecting device 102 rotates. At this time, the rotation can be counted once.

Figure 9A:
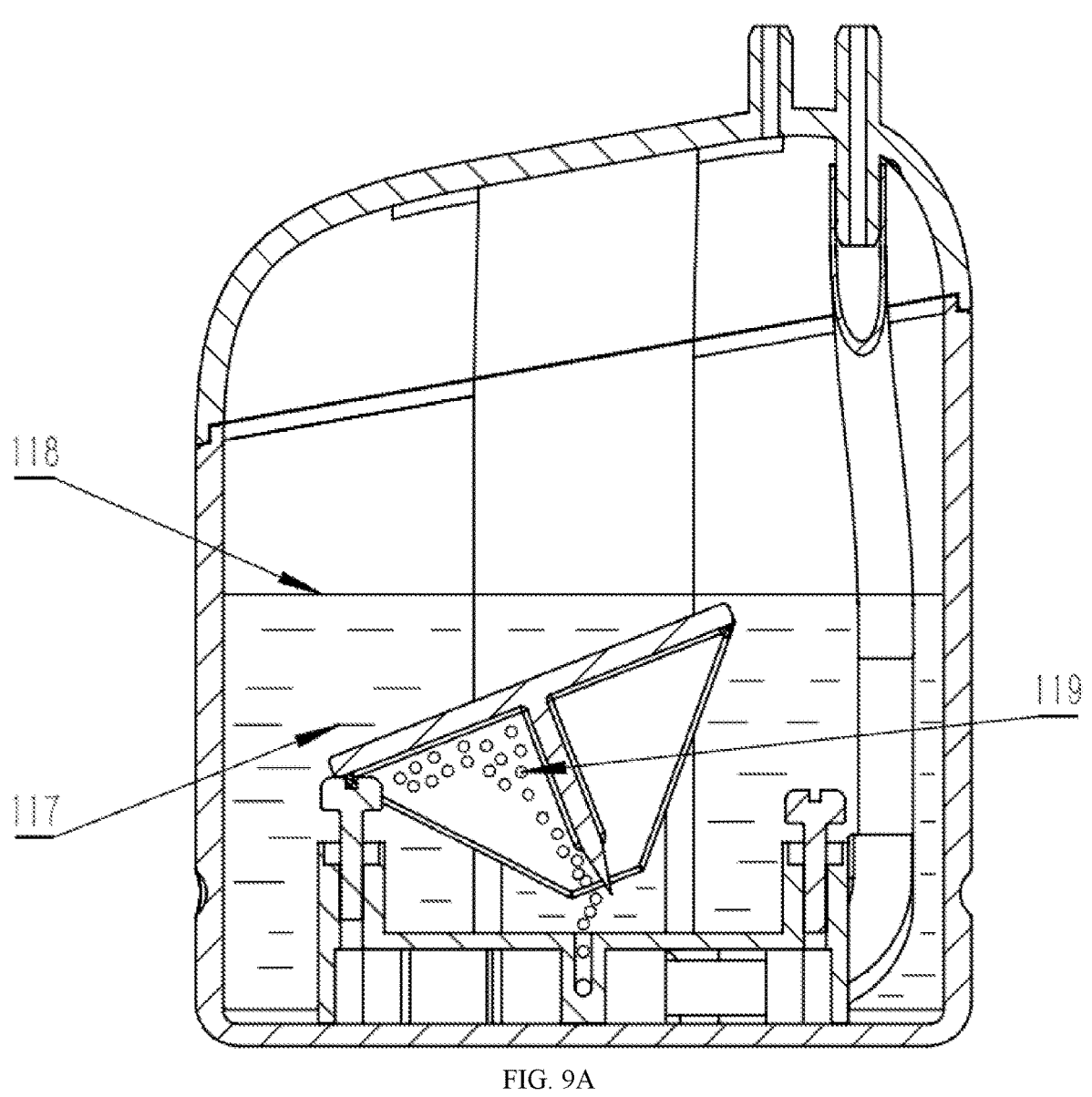
FIG. 9A is a schematic diagram A of a gas measuring apparatus according to embodiments of the present disclosure.
Figure 9B:
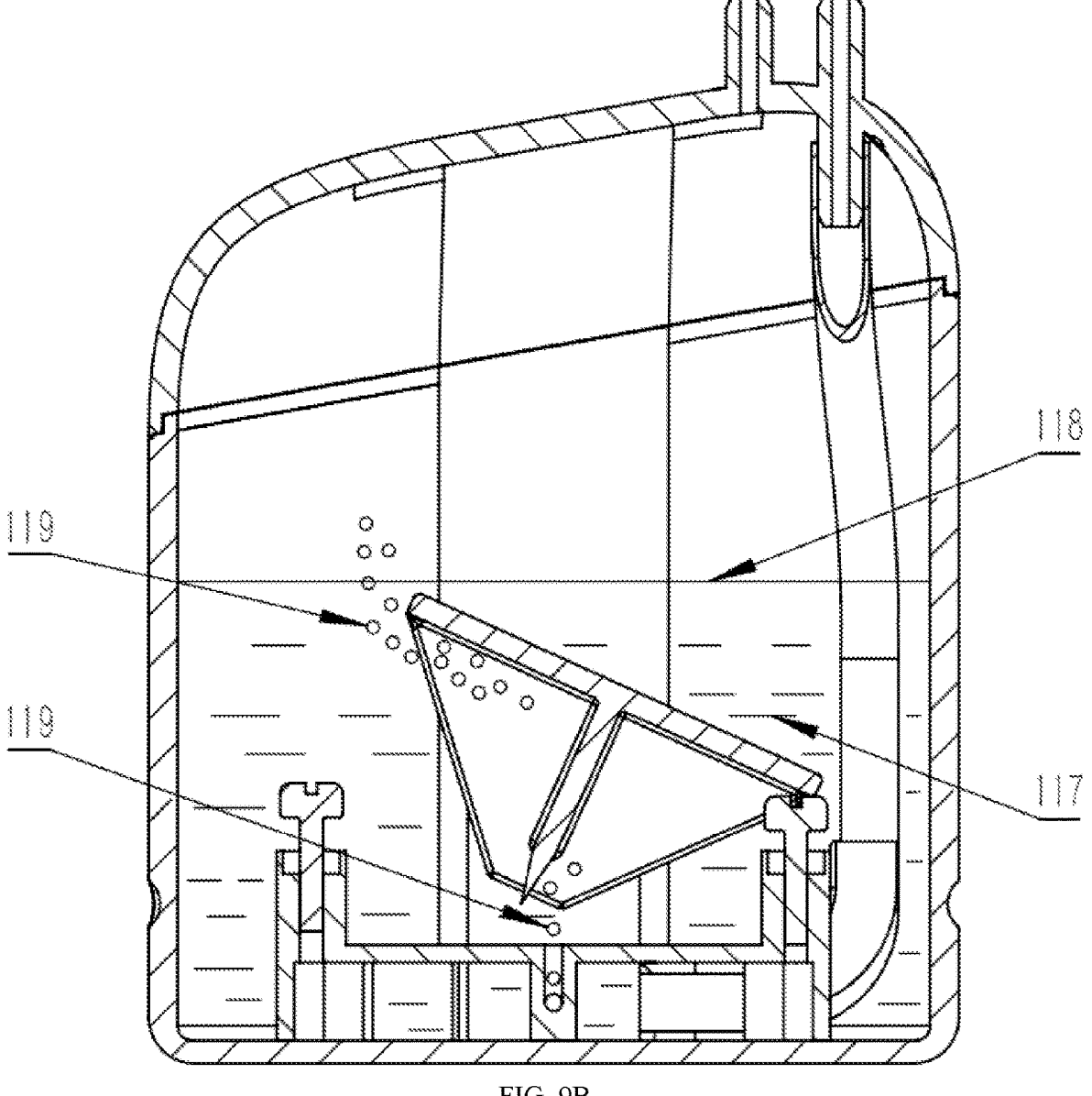
FIG. 9B is a schematic diagram B of a gas measuring apparatus according to embodiments of the present disclosure.
Figure 9C:
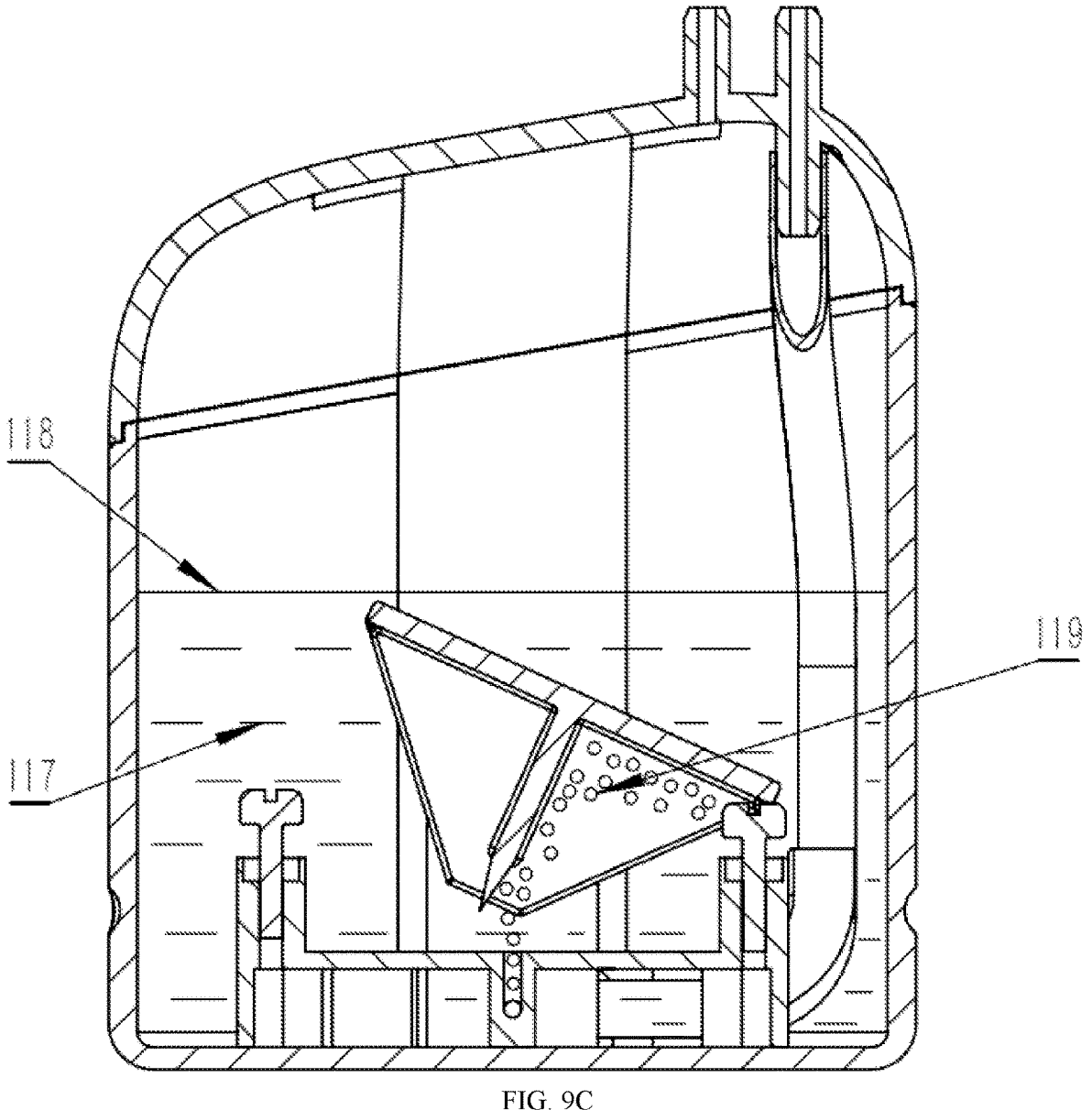
FIG. 9C is a schematic diagram C of a gas measuring apparatus according to embodiments of the present disclosure.
Figure 9D:
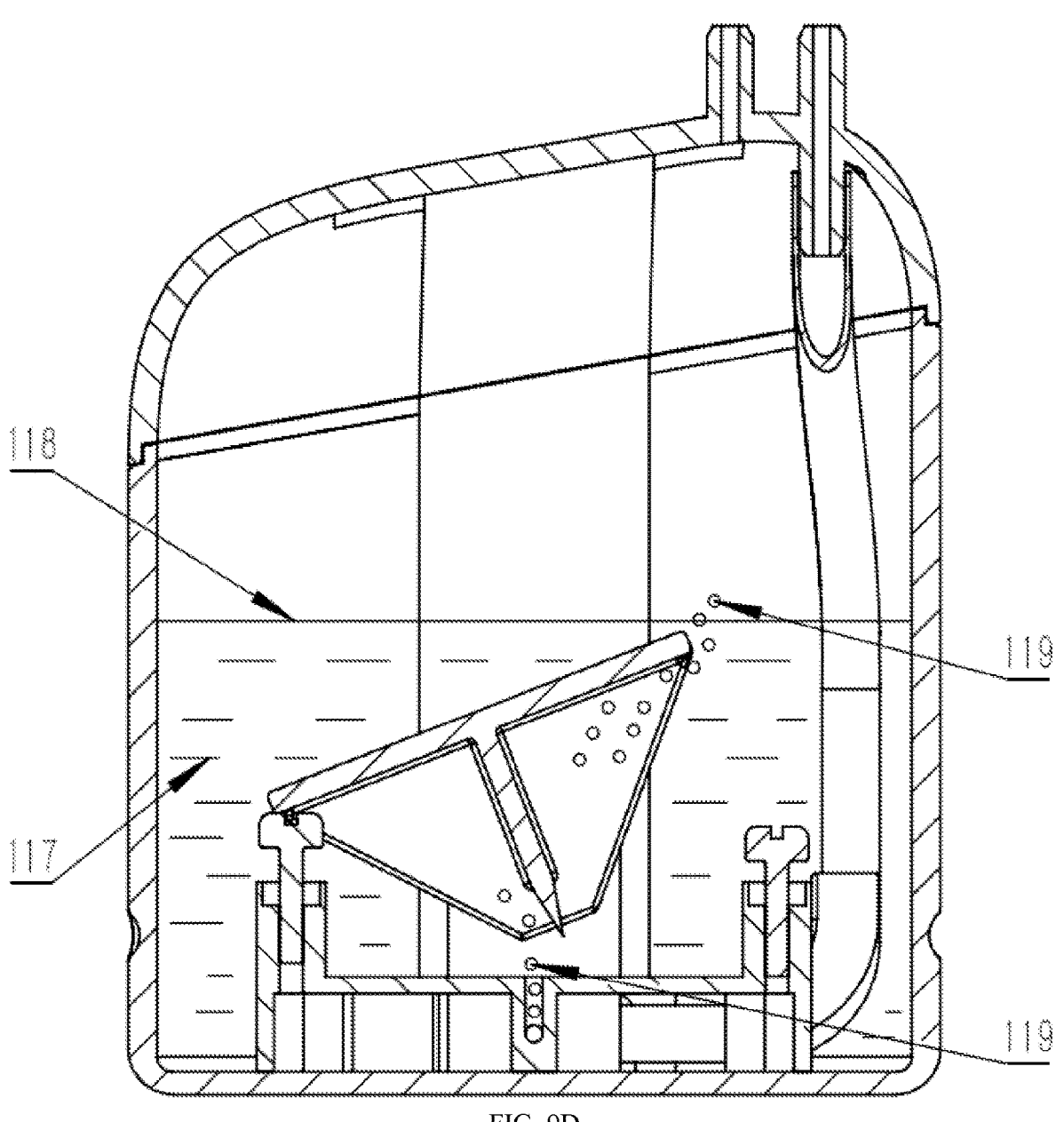
FIG. 9D is a schematic diagram D of a gas measuring apparatus according to embodiments of the present disclosure.

FIG. 9A is a schematic diagram A of a gas measuring apparatus according to embodiments of the present disclosure. FIG. 9B is a schematic diagram B of a gas measuring apparatus according to embodiments of the present disclosure. FIG. 9C is a schematic diagram C of a gas measuring apparatus according to embodiments of the present disclosure. FIG. 9D is a schematic diagram D of a gas measuring apparatus according to embodiments of the present disclosure. As shown in FIGS. 9A-9D, the working principle of the gas measuring apparatus 100 is as follows. Gas enters the liquid medium 117 from the gas inlet 106 in the form of bubbles 119, and rises in the liquid medium 117 to enter a gas entrapping compartment. Here, as an example, the edge of the first gas entrapping compartment 1021 collides with the first positioning holder 104, so that the first gas entrapping compartment 1021 stays right above the gas inlet 106. That is, as an example, the bubbles 119 enter the first gas entrapping compartment 1021 first. As shown in FIG. 9A, as the bubbles 119 accumulate, the buoyancy generated by the bubbles 119 in the first gas entrapping compartment 1021 is increasing. When the buoyancy generated by the bubbles 119 in the first gas entrapping compartment 1021 is greater than the rotating force of the gas collecting device 102, the gas collecting device 102 rotates, so that the first gas entrapping compartment 1021 is lifted close to the liquid medium level 118, as shown in FIG. 9B, so the bubbles 119 in the first gas entrapping compartment 1021 are released into the upper space inside the chamber 101. At the same time, the second gas entrapping compartment 1022 rotates right above the gas inlet 106. The bubbles 119 rise into the second gas entrapping compartment 1022. The edge of the second gas entrapping compartment 1022 collides with the second positioning holder 105, so that the second gas entrapping compartment 1022 stays right above the gas inlet 106. As shown in FIG. 9C, as the bubbles 119 accumulate, the buoyancy generated by the bubbles 119 in the second gas entrapping compartment 1022 is increasing. When the buoyancy generated by the bubbles 119 in the second gas entrapping compartment 1022 is greater than the rotating force of the gas collecting device 102, the gas collecting device 102 rotates, so that the second gas entrapping compartment 1022 is lifted close to the liquid medium level 118, as shown in FIG. 9D, so the bubbles 119 in the second gas entrapping compartment 1022 are released into the upper space inside the chamber 101. At the same time, the first gas entrapping compartment 1021 rotates right above the gas inlet 106. The bubbles 119 rise into the first gas entrapping compartment 1021. The edge of the first gas entrapping compartment 1021 collides with the first positioning holder 104, so that the first gas entrapping compartment 1021 stays right above the gas inlet 106, continuing to accumulate the bubbles 119.

The liquid medium 117 may be water or other liquid medium that does not dissolve the gas to be measured and does not generate gas.

In an embodiment, the gas measuring apparatus 100 further includes an input port 113 and a gas inlet pipeline 108. Gas enters the gas inlet pipeline 108 from the input port 113 and enters the gas inlet 106 through the gas inlet pipeline 108.

The fixing frame 103 may be rotatably connected with the gas collecting device 102 in such a manner that a hole cooperates with a shaft or in other manners. As long as the rotating connection is realized, the way of the rotating connection is not specifically limited in the present disclosure.

The first positioning holder 104 and the second positioning holder 105 may be both of a block structure or a strip structure. As long as the first positioning holder 104 and the second positioning holder 105 can collide with the gas collecting device 102 to achieve the purpose of limiting, the structure of the first positioning holder 104 and the second positioning holder 105 is not specifically limited in the present disclosure.

Therefore, the gas measuring apparatus 100 is provided with two gas entrapping compartments, so that the bubbles 119 emerged from the gas inlet 106 enter one of the two gas entrapping compartments, and when the gas collecting device 102 rotates to release the gas in the gas entrapping compartment after the accumulated bubble volume reaches a preset volume, the bubbles 119 emerged from the gas inlet enter the other one of the two gas entrapping compartments in turn, thus the gas leakage is avoided and the accuracy of gas measurement results are improved. In addition, the first positioning holder 104 and the second positioning holder 105 are provided, so that the rotation angle of the gas collecting device 102 can be limited, thus the center of gravity position of the gas collecting device 102 when rotate to a preset angle is accurately limited, the buoyancy of the gas required for rotating the gas collecting device 102 is accurately limited, and the volume of the gas in the gas entrapping compartment corresponding to one rotation is accurately limited, so as to further improve the accuracy of the gas measurement.

In an embodiment of the present disclosure, the first gas entrapping compartment 1021 and the second gas entrapping compartment 1022 are symmetrically arranged, so that the gas collecting device 102 can rotate each time under the effect of the buoyancy generated by the same volume of the gas, so as to improve the accuracy of the gas measurement.

In an embodiment of the present disclosure, the first positioning holder 104 includes a first fixing unit 1041 and a first stroke adjusting unit 1042. The first fixing unit 1041 is fixedly connected with the fixing frame 103. The first stroke adjusting unit 1042 is located above the first fixing unit 1041, and is movably connected to the first fixing unit 1041 up and down, so as to realize the height adjustment of the first positioning holder 104 and adjust the collision position with the first gas entrapping compartment 1021.

Specifically, the first stroke adjusting unit 1042 may be screwed with the first fixing unit 1041, and the height of the first stroke adjusting unit 1042 can be raised or lowered by screw rotation. The first stroke adjusting unit 1042 may also be buckled with the first fixing unit 1041, and the height of the first stroke adjusting unit 1042 can be raised or lowered by adjusting the clamping position of a buckle. As long as the first stroke adjusting unit 1042 and the first fixing unit 1041 can be movably connected up and down, the connection form of the first stroke adjusting unit 1042 and the first fixing unit 1041 is not specifically limited in the present disclosure.

Similarly, the second positioning holder 105 includes a second fixing unit 1051 and a second stroke adjusting unit 1052. The second fixing unit 1051 is fixedly connected with the fixing frame 103. The second stroke adjusting unit 1052 is located above the second fixing unit 1051, and is movably connected to the second fixing unit 1051 up and down, so as to realize the height adjustment of the second positioning holder 105 and adjust the collision position with the first gas entrapping compartment 1021.

Specifically, the second stroke adjusting unit 1052 may be screwed with the second fixing unit 1051, and the height of the second stroke adjusting unit 1052 can be raised or lowered by screw rotation. The second stroke adjusting unit 1052 may also be buckled with the second fixing unit 1051, and the height of the second stroke adjusting unit 1052 can be raised or lowered by adjusting the clamping position of a buckle. As long as the second stroke adjusting unit 1052 and the second fixing unit 1051 can be movably connected up and down, the connection form of the second stroke adjusting unit 1052 and the second fixing unit 1051 is not specifically limited in the present disclosure.

The heights of the first positioning holder 104 and the second positioning holder 105 are adjustable, so that the collision positions with the gas collecting device 102 is adjustable. The rotation angle of the gas collecting device 102 is adjustable. The center of gravity of the gas collecting device 102 after stopping rotating due to the collision with the first positioning holder 104 and the second positioning holder 105 is adjustable. The buoyancy of the gas required for rotating the gas collecting device 102 is adjustable. The volume of the gas in the gas entrapping compartment corresponding to one rotation is adjustable. That is, the resolution of the gas measuring apparatus 100 is adjustable, thereby the accuracy of the resolution of the gas measuring apparatus 100 is improved.

In an embodiment of the present disclosure, the gas collecting device 102 further includes a partition 1023 and a bubble steering unit 107. The partition 1023 is configured to separate the first gas entrapping compartment 1021 from the second gas entrapping compartment 1022, so as to realize the symmetrical separation of the first gas entrapping compartment 1021 and the second gas entrapping compartment 1022. The bubble steering unit 107 may be a sheet structure or a block structure and is fixedly connected to the partition 1023 for blocking the deviation of the rising route of the bubbles.

Specifically, the bubble steering unit 107 may be fixedly connected with the partition 1023 by bonding. The bubble steering unit 107 may be integrally formed with the partition 1023 during manufacture. The connection form of the bubble steering unit 107 and the partition 1023 is not specifically limited in the present disclosure.

The bubble steering unit 107 is provided, so as to block the deviation of the rising route of the bubbles, and prevent the bubbles from simultaneously entering the first gas entrapping compartment 1021 and the second gas entrapping compartment 1022.

In an embodiment of the present disclosure, as shown in FIG. 8, the shape of the cross section of the bubble steering unit 107 parallel to the side wall of the gas collecting device may be an inverted triangle, thereby the space for the deviation of the rising route of the bubbles is increased, and the ability of the gas measuring apparatus 100 to resist external vibration and other interferences is improved.

The shape of the cross section of the bubble steering unit 107 parallel to the side wall of the gas collecting device may also be an inverted trapezoid, an inverted triangle with rounded corners, an inverted trapezoid with rounded corners, etc., as long as the space for the deviation of the rising route of bubbles can be increased. The shape of the cross section of the bubble steering unit 107 parallel to the side wall of the gas collecting device is not specifically limited in the present disclosure.

In an embodiment of the present disclosure, the gas inlet 106 may be a circular through-hole. One end of the gas inlet 106 is connected with one end of the gas inlet pipeline 108, and gas enters from the other end of the gas inlet pipeline 108 and emerges from the other end of the gas inlet 106. Moreover, the diameter of the circular through-hole is set to be smaller than the internal diameter of the gas inlet pipeline 108.

The diameter of the circular through-hole is set to be smaller than the internal diameter of the gas inlet pipeline 108, so that the gas enters the circular through-hole with a smaller diameter from the gas inlet pipeline 108 with a larger diameter, the pressure of the gas is increased, and the bubbles smoothly rise into the gas entrapping compartment. At the same time, the diameter of the gas inlet 106 is reduced, so that the diameter of the bubble emerged from the gas inlet 106 is reduced, thus the probability of bubble breakage and deviation of the rising route of the bubbles is reduced, the probability that the bubbles rise to the gas entrapping compartment smoothly is increased, so as to improve the accuracy of gas measurement.

In an embodiment of the present disclosure, the gas collecting device 102 further includes a partition 1023, a rod-shaped structure 109 and a transmitter 110. The partition 1023 is configured to separate the first gas entrapping compartment 1021 from the second gas entrapping compartment 1022, so as to realize the symmetrical separation of the first gas entrapping compartment 1021 and the second gas entrapping compartment 1022. One end of the rod-shaped structure 109 is connected with the partition 1023, and swings with the gas collecting device 102. The transmitter 110 is fixedly installed at the other end of the rod-shaped structure 109, and is configured to send a swing signal of the gas collecting device.

The transmitter 110 may be a transmitter of a sensor, such as a Hall sensor, a photosensitive sensor, a light sensor counter, an NFC, etc., separated from the receiver, as long as the transmitter is a transmitter of a sensor separated from the receiver. The type of the transmitter 110 is not specifically limited in the present disclosure.

The transmitter 110 is used, so as to obtain the swing signal of the gas collecting device and send the swing signal. The swing times can be automatically calculated by receiving the swing signal, thus the probability of miscalculation times is reduced, so as to further improve the accuracy of gas measurement.

In an embodiment of the present disclosure, the gas measuring apparatus 100 further includes a receiver, which is communicated with the transmitter 110 and receives the swing signal sent by the transmitter 110, so as to automatically calculate the swing times. Thereby, the probability of miscalculation times is reduced, so as to further improve the accuracy of gas measurement.

In an embodiment of the present disclosure, the outline of the rod-shaped structure 109 is streamlined, so that the influence of the movement of the rod-shaped structure 109 on the liquid medium 117 is reduced, the interference to the movement route of the bubbles is reduced, and the accuracy of the gas measurement is further improved.

In an embodiment of the present disclosure, the receiver is located outside the chamber 101. The inner bottom surface of the chamber 101 includes a concave part 116, and the concave part 116 provides an accommodation space for one end of the rod-shaped structure 109 where the transmitter 110 is installed, so that the rod-shaped structure 109 passes through the concave part 116 when swinging to the bottom of the chamber 101, thereby the volume of the chamber 101 is reduced. At the same time, the concave part 116 forms a bulge on the outside of the chamber 101. The receiver can be installed at the bulge. Therefore, the contact area between the transmitter 110 and the receiver when the transmitter passes through the concave part 116 can be increased, and the distance between the transmitter 110 and the receiver when the transmitter passes through the concave part 116 can be reduced, so that the swing signal can be transmitted more accurately, and the accuracy of the gas measurement can be further improved.

In an embodiment of the present disclosure, the material of the chamber 101 includes a transparent material, which is convenient for users to observe the movement of the internal components of the chamber 101.

Specifically, the material of the chamber 101 may be polycarbonate (PC) or other transparent materials that can contain the liquid medium 117, as long as the material is a transparent material that can contain the liquid medium 117. The material of the chamber 101 is not specifically limited in the present disclosure.

In an embodiment of the present disclosure, the chamber 101 includes a maximum liquid level scale line and a minimum liquid level scale line. The maximum liquid level scale line and the minimum liquid level scale line are used to indicate the liquid level of the liquid medium 117 contained in the chamber 101, so that the liquid level of the liquid medium 117 contained in the chamber 101 is accurately located between the maximum liquid level scale line and the minimum liquid level scale line. Moreover, it is also convenient for users to observe whether the actual liquid level of the liquid medium 117 is between the maximum liquid level scale line and the minimum liquid level scale line, thus ensuring the measurement accuracy of the gas measuring apparatus 100.

In an embodiment of the present disclosure, the chamber 101 includes a first curved strip-like depression 114. The first curved strip-like depression 114 is located at the outer side of the chamber. The shape of the cross section of the first curved strip-like depression 114 perpendicular to the chamber 101 may include an arc line.

The first curved strip-like depression 114 is provided, and the shape of the cross section of the first curved strip-like depression 114 perpendicular to the chamber 101 includes an arc line. Therefore, the chamber 101 can be buckled with a convex structure of a desktop or other apparatuses, so that the gas measuring apparatus 100 can be stably placed on the desktop or other apparatuses, and a stable measuring environment for the gas measuring apparatus 100 can be provided, so as to further improve the accuracy of gas measurement.

In an embodiment, the chamber 101 further includes a second curved strip-like depression 115. The second curved strip-like depression 115 is located at the outer side of the chamber. The shape of the cross section of the second curved strip-like depression 115 perpendicular to the chamber 101 may include an arc line.

The second curved strip-like depression 115 is provided, and the shape of the cross section of the second curved strip-like depression 115 perpendicular to the chamber 101 includes an arc line. Therefore, the firmness of buckling the chamber 101 with the convex structure of the desktop or other apparatuses is increased, so that the stability of the gas measuring apparatus 100 placed on the desktop or other apparatuses is further improved, a more stable measuring environment for the gas measuring apparatus 100 is provided, so as to further improve the accuracy of the gas measurement.

The chamber 101 can further include more curved strip-like depressions, and the number of the curved strip-like depressions can be set according to specific application scenarios. The number of the curved strip-like depressions is not specifically limited in the present disclosure.

In an embodiment of the present disclosure, the gas measuring apparatus 100 further includes a pipeline guiding unit 111, which is fixedly connected with the fixing frame 103. The pipeline guiding unit 111 can be a tubular structure, a grooved structure or both, so as to surround and/or semi-surround the gas inlet pipeline 108, so that the gas inlet pipeline 108 is laid along the pipeline guiding unit and the gas inlet pipeline 108 is fixed, so as to prevent the interference such as vibration resulted from the gas flowing in the gas inlet pipeline 108. A stable measuring environment is provided for the gas measuring apparatus 100, thereby further improving the accuracy of gas measurement.

In an embodiment of the present disclosure, the gas measuring apparatus 100 further includes a gas outlet 112, which is located at the upper part of the chamber 101 and is configured to release the gas emerged from the liquid medium 117, thereby facilitating the collection and the reuse of the gas emerged from the liquid medium 117.

In an embodiment of the present disclosure, the chamber 101 may include a bottom chamber 1011 and a top cover 1012. The bottom chamber 1011 and the top cover 1012 may be detachably connected, for example, they may be buckled or screwed, as long as they are detachably connected. The connection form of the bottom chamber 1011 and the top cover 1012 is not specifically limited in the present disclosure.

The chamber 101 includes the bottom chamber 1011 and the top cover 1012, and the bottom chamber 1011 and the top cover 1012 are detachably connected, which is convenient for users to observe, repair and maintain the components inside the gas measuring apparatus 100, and which is also convenient to manufacture the chamber 101 at the same time.

The above is only the preferred embodiments of the present disclosure, and it is not intended to limit the present disclosure. Any modifications and equivalent substitutions made within the spirit and principle of the present disclosure should be included in the scope of protection of the present disclosure.

What is claimed is:

1. A gas measuring apparatus, comprising:
a gas collecting device, comprising two gas entrapping compartments;
a fixing frame, which is rotatably connected with the gas collecting device;
positioning holders, each of which is located below a corresponding one of the two gas entrapping compartments and is configured to limit a rotation angle of the gas collecting device by colliding with an edge of the corresponding one of the two gas entrapping compartments;
a chamber, which accommodates the gas collecting device, the fixing frame, the positioning holders and a liquid medium; and
a gas inlet, which is located below the gas collecting device, wherein bubbles emerge from the gas inlet and rise into one of the two gas entrapping compartments, as the bubbles accumulate, the liquid medium in the one of the two gas entrapping compartments is gradually discharged, and the gas collecting device rotates under a buoyancy effect of the bubbles which are accumulated, so that the bubbles emerged from the gas inlet rise into an other one of the two gas entrapping compartments,
wherein each of the positioning holders comprises:
a fixing unit, which is fixedly connected with the fixing frame; and
a stroke adjusting unit, which is located above the fixing unit and is movably connected to the fixing unit up and down, so as to realize a height adjustment of a corresponding one of the positioning holders and adjust a collision position with a corresponding one of the two gas entrapping compartments.

2. The gas measuring apparatus according to claim 1, wherein the two gas entrapping compartments are symmetrically arranged.

3. The gas measuring apparatus according to claim 2, wherein the gas inlet comprises a circular through-hole, one end of the gas inlet is connected with one end of a gas inlet pipeline, and gas enters from an other end of the gas inlet pipeline and emerges from an other end of the gas inlet and wherein a diameter of the circular through-hole is smaller than an internal diameter of the gas inlet pipeline.

4. The gas measuring apparatus according to claim 1, wherein the gas collecting device further comprises:

a partition, which is configured to separate the two gas entrapping compartments, so as to realize a symmetrical separation of the two gas entrapping compartments; and a bubble steering unit, which comprises a sheet structure or a block structure, the bubble steering unit is fixedly connected to the partition of the two gas entrapping compartments for blocking a deviation of a rising route of the bubbles.

5. The gas measuring apparatus according to claim 4, wherein a cross section of the bubble steering unit parallel to a side wall of the gas collecting device is of an inverted triangle shape.

6. The gas measuring apparatus according to claim 1, wherein the gas collecting device further comprises:

a partition, which is configured to separate the two gas entrapping compartments, so as to realize a symmetrical separation of the two gas entrapping compartments;

a rod-shaped structure, one end of which is connected with the partition and swings with the gas collecting device; and a transmitter, which is fixedly installed at an other end of the rod-shaped structure and is configured to send a swing signal of the gas collecting device.

7. The gas measuring apparatus according to claim 1, wherein the gas inlet comprises a circular through-hole, one end of the gas inlet is connected with one end of a gas inlet pipeline, and gas enters from an other end of the gas inlet pipeline and emerges from an other end of the gas inlet and wherein a diameter of the circular through-hole is smaller than an internal diameter of the gas inlet pipeline.

8. The gas measuring apparatus according to claim 7, wherein the gas measuring apparatus further comprises a pipeline guiding unit, which is fixedly connected with the fixing frame, wherein the pipeline guiding unit comprises a tubular structure and/or a groove- shaped structure for surrounding and/or semi-surrounding the gas inlet pipeline, so that the gas inlet pipeline is laid along the pipeline guiding unit.

9. The gas measuring apparatus according to claim 1, wherein an outline of the rod-shaped structure is streamlined.

10. The gas measuring apparatus according to claim 1, wherein the gas measuring apparatus further comprises a receiver, which communicates with the transmitter and receives the swing signal sent by the transmitter.

11. The gas measuring apparatus according to claim 10, wherein the receiver is located outside the chamber and wherein an inner bottom surface of the chamber comprises a concave part, and the concave part provides an accommodation space for one end of the rod-shaped structure where the transmitter is installed, so that the rod-shaped structure passes through the concave part when swinging to a bottom of the chamber.

12. The gas measuring apparatus according to claim 11, wherein the concave part forms a bulge on an outside of the chamber, the receiver is installed at the bulge, to increase contact area between the transmitter and the receiver when the transmitter passes through the concave part, and to reduce a distance between the transmitter and the receiver when the transmitter passes through the concave part.

13. The gas measuring apparatus according to claim 1, wherein a material of the chamber comprises a transparent material.

14. The gas measuring apparatus according to claim 1, wherein the chamber comprises:

a curved strip-like depression, which is located at an outer side of the chamber;

wherein an outline of a cross section of the curved strip-like depression perpendicular to the chamber comprises an arc line.

15. The gas measuring apparatus according to claim 1, wherein the gas measuring apparatus further comprises a gas outlet, which is located at an upper part of the chamber and is configured to release gas that has emerged from the liquid medium.

16. The gas measuring apparatus according to claim 1, wherein the chamber comprises a bottom chamber and a top cover, and the bottom chamber and the top cover are detachably connected.

* * * * *